United States Patent
Suh et al.

(10) Patent No.: US 8,227,496 B2
(45) Date of Patent: *Jul. 24, 2012

(54) USE OF 4-[(4-THIAZOLYL)PHENOXY] ALKOXY-BENZAMIDINE DERIVATIVES FOR TREATMENT OF OSTEOPOROSIS

(75) Inventors: Hong-Suk Suh, Kumjung-Gu (KR); Jin Soo Lee, Yongin-si (KR); Pan-Soo Kim, Anyang-i si (KR); Yun-Ha Hwang, Ansan-si (KR); Jei Man Ryu, Anyang-si (KR); Yong-Ho Chung, Anyang-si (KR); Eun-Joo Kim, Yusong-gu (KR); Do-Hui Kim, Songnam-si (KR); Yong-Youp Park, Kumjung-gu (KR)

(73) Assignee: Dong Wha Pharmaceutical Co., Ltd, Seoul (KR)

( * ) Notice: Subject to any disclaimer, the term of this patent is extended or adjusted under 35 U.S.C. 154(b) by 34 days.

This patent is subject to a terminal disclaimer.

(21) Appl. No.: 12/689,878

(22) Filed: Jan. 19, 2010

(65) Prior Publication Data

US 2010/0120875 A1    May 13, 2010

Related U.S. Application Data

(63) Continuation of application No. 10/484,094, filed as application No. PCT/KR02/00463 on Mar. 19, 2002, now Pat. No. 7,662,840.

(30) Foreign Application Priority Data

Jul. 19, 2001 (KR) .................................. 2001-43490

(51) Int. Cl.
| | | |
|---|---|---|
| *A01N 43/78* | (2006.01) | |
| *A01N 37/52* | (2006.01) | |
| *A61K 31/425* | (2006.01) | |
| *A61K 31/155* | (2006.01) | |
| *C07D 277/60* | (2006.01) | |
| *C07D 416/00* | (2006.01) | |
| *C07C 249/00* | (2006.01) | |
| *C07C 251/00* | (2006.01) | |
| *C07C 259/00* | (2006.01) | |
| *C07C 291/00* | (2006.01) | |

(52) U.S. Cl. ........ 514/365; 514/631; 514/878; 548/150; 564/229

(58) Field of Classification Search ................... 514/365, 514/631, 878; 548/150; 564/229
See application file for complete search history.

(56) References Cited

U.S. PATENT DOCUMENTS

| 5,451,700 | A | | 9/1995 | Morrissey et al. | |
|---|---|---|---|---|---|
| 5,994,329 | A | * | 11/1999 | Daifotis et al. | ................ 514/108 |
| 6,124,314 | A | * | 9/2000 | Cameron et al. | ............... 514/307 |
| 6,150,390 | A | | 11/2000 | Suh et al. | |

FOREIGN PATENT DOCUMENTS

| AU | 2002241361 | 5/2007 |
|---|---|---|
| KR | 98-071076 | 10/1998 |
| KR | 10-0454767 | 10/2004 |

OTHER PUBLICATIONS

EP 02707300.6-1216 Exam Report, Feb. 26, 2007, Dong Wha Pharm Ind. Co., Ltd.
Ford-Hutchinson, A.W., et al., Nature (London), 286, 264-265, 1980.
Meghji, S., et al., Calcif. Tiss. Int., 36, 139-149, 1988.
Mundy, G.R., et al., J. Bio. Chem., 268, 10087-10094, 1993.
Bonewald, L. F., et al., J. Bone Miner. Res., 11, 1619-1627, 1996.
Bonewald, L.F. et al., J. Bone Miner. Res., 11, 521-529, 1996.
Gregg Wesolowski et al., Experimental Cell Research, 219, 679-686, 1995.
Eijiro Jimi, et al., Endocrinology, 137, p. 2187-2190, 1996.
Y. Wada, et al., Bone, 22, 479-485, 1998.
Sung-Eun Lee, "Design, Syntheses, and Evaluation of the Functional Molecules for the Treatment of the LTB4 related disease and electroluminescent device," Doctoral Dissertation, Department of Chemistry, Graduate School of Arts and Science, Busan Univ., South Korea, Aug. 1999.

* cited by examiner

*Primary Examiner* — Sreeni Padmanabhan
*Assistant Examiner* — Kendra D Carter
(74) *Attorney, Agent, or Firm* — Arent Fox LLP

(57) ABSTRACT

A method of treating osteoporosis comprising administering to a subject a composition comprising a compound, 4-{5-[4-(5-isopropyl-2-methyl-1,3-thiazol-4-yl)phenoxy]pentoxy}-benzamidine or a salt thereof, is described. A method of inhibiting osteoclast activity and stimulating osteoblast activity in a subject also is described.

16 Claims, No Drawings

USE OF 4-[(4-THIAZOLYL)PHENOXY] ALKOXY-BENZAMIDINE DERIVATIVES FOR TREATMENT OF OSTEOPOROSIS

CROSS REFERENCE TO RELATED APPLICATION

This is a continuation of U.S. patent application Ser. No. 10/484,094, filed Jan. 16, 2004, and claiming the benefit of priority to PCT/KR 2002/00463 filed Mar. 19, 2002 and KR 2001-43490 filed Jul. 19, 2001.

TECHNICAL FIELD

The present invention relates to a pharmaceutical composition containing 4-[(4-thiazolyl)-phenoxy]alkoxy-benzamidine derivatives represented by the following formula 1 for the prevention and treatment of osteoporosis and more particularly, to the pharmaceutical composition containing 4-{5-[4-(5-isopropyl-2-methyl-1,3-thiazol-4-yl)phenoxy]pentoxy}-benzamidine (hereinafter referred to as "DW1352") or N-hydroxy-4-{5-[4-(5-isopropyl-2-methyl-1,3-thiazol-4-yl)phenoxy]pentoxy}-benzamidine (hereinafter referred to as "DW1350") represented by the following formula 1, which is reported to have leukotriene-$B_4$ (hereinafter referred to as "LTB-4") receptor antagonism for the prevention and treatment of osteoporosis.

Formula 1

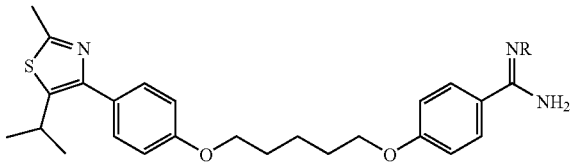

Wherein, R is a hydrogen atom or a hydroxy group.

BACKGROUND ART

Bone is the structural material of the body's framework and serves to maintain the necessary bone mass and structure. Bone contains calcium ($Ca^{2+}$) and plays an important role in maintaining the calcium level in the blood. To this end, the growth of bone is a metabolic balance between the activity of osteoblasts and osteoclasts in the bone remodelling cycle.

When the balance between bone absorption and bone formation is disrupted, the amount of bone tissue replaced by osteoblasts fails to match that absorbed by osteoclasts, thus leading to osteoporosis, a common condition to cause loss of bone density or bone mass. This disease is frequently occurring in middle-aged or elderly women.

To date, the established strategy has been to produce drugs capable of preventing bone loss by inhibiting osteoclastic bone absorption. Attempts to develop alternative therapies, such as LTB-4 receptor antagonist, have been made but their development towards effective anti-osteoporotic agent has been unsuccessful due to insufficient inhibition on osteoclastic bone absorption. Therefore, there is an urgent need for new osteoporosis therapies aimed at suppressing osteoclastic bone absorption.

4-[(4-thiazolyl)-phenoxy]alkoxy-benzamidine derivative, together with its process for preparation, has been already known as leukotriene-$B_4$ receptor antagonist (Lee Sung-eun, *Synthesis and Biological Activity of Natural Products and Designed New Hybrid Compounds for the Treatment of $LTB_4$ Related Disease*, Ph.D thesis, Graduate School of Pusan Univ., August 1999).

The natural product LTB-4 is one of arachidonate metabolites formed via 5-lipoxygenase pathway [Ford-Hutchinson, A. W. et al., *Nature* (London), 286, 264-265, 1980].

The recent studies have focused on the influence of arachidonate metabolites on the bone tissue metabolism.

5-lipoxygenase metabolites produced from osteoblasts are found to stimulate bone absorption (Meghji, S. et. al., *Calcif. Tiss. Int.* 36, 139-149, 1988); the interstitial cells C433 obtained from a giant cell tumor is involved in producing 5-lipoxygenase metabolites to increase the counts and activity of osteoblasts (Mundy, G. R., *J. Bio. Chem.* 268, 10087-10094, 1993); the bone absorption function may be stimulated with the addition of synthetic LTB-4 during the cultivation process of bone tissue (Bonewald, L. F., *J Bone Miner. Res.* 11, 521-529, 1996); and Both in vitro and in vivo studies have demonstrated that LTB-4 induces the bone absorption via production of osteoclasts (Bonewald, L. F., *J. Bone Miner. Res.* 11, 1619-1627, 1996).

Currently, many studies have been under way with the conception that some compound showing an antagonistic action against LTB-4 receptor may affect the embolic diseases of bone tissue.

The inventors have conducted intensive studies to identify a number of diverse-structure compounds useful as effective LTB-4 receptor antagonists, aimed at suppressing osteoclastic bone absorption or stimulating osteoblastic bone formation. In consequence it has been identified that 3-amino-1,2-benzoisoxazole derivative represented by the following formula 2 is effective in the prevention and treatment of osteoporosis, while exerting antagonistic action against LTB-4 receptor. The inventors filed a patent application of such compound dated Feb. 4, 1998 (KR 98-3138).

Formula 2

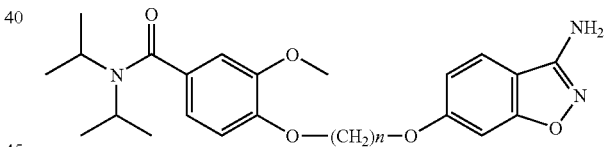

Wherein, n is an integer of 3~5.

In an effort to identify alternative osteoporosis therapies, the inventors have tested the inhibitory action of 4-[(4-thiazolyl)-phenoxy]alkoxy-benzamidine derivatives as LTB-4 receptor antagonist; among these derivatives, such compound as 4-{5-[4-(5-isopropyl-2-methyl-1,3-thiazol-4-yl)phenoxy]pentoxy}-benzamidine or N-hydroxy-4-{5-[4-(5-isopropyl-2-methyl-1,3-thiazol-4-yl)phenoxy]pentoxy}-benzamidine is found to be significantly effective in preventing bone loss by inhibiting osteoclastic bone absorption. Thus, the present invention has been finally completed.

DISCLOSURE OF THE INVENTION

The present invention relates to the therapeutic use of a pharmaceutical composition containing 4-{5-[4-(5-isopropyl-2-methyl-1,3-thiazol-4-yl)phenoxy]pentoxy}-benzamidine or N-hydroxy-4-{5-[(4-(5-isopropyl-2-methyl-1,3-thiazol-4-yl)phenoxy]pentoxy}-benzamidine represented by the following formula 1 for the prevention and treatment of osteoporosis.

Formula 1

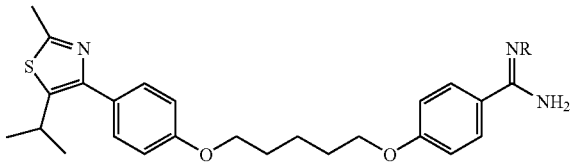

Wherein, R is a hydrogen atom or a hydroxy group.

4-[(4-thiazolyl)-phenoxy]alkoxy-benzamidine derivatives may be prepared by the conventional method (Lee Sung-eun, *Synthesis and Biological Activity of Natural Products and Designed New Hybrid Compounds for the Treatment of LTB$_4$ Related Disease*, Ph.D thesis, Graduate School of Pusan Univ., August 1999). Compounds of the present invention represented by the formula 1 may be also used with pharmaceutically acceptable salts using the following materials: inorganic acids (hydrochloric acid, bromic acid, sulfuric acid and phosphoric acid); organic acids (citric acid, acetic acid, lactic acid, tartaric acid, fumaric acid, formic acid, propionic acid, oxalic acid, trifluoroacetic acid, methanesulfonic acid, benzoic acid, maleic acid, gluconic acid, glycollic acid, succinic acid, 4-toluenesulfonic acid, galacturonic acid, embonic acid, glutamic acid or aspartic acid. According to the present invention, it is preferred to employ hydrochloric acid as inorganic acid and methanesulfonic acid as organic acid.

The anti-osteoporotic composition of the present invention may be applied in a therapeutically effective dose via various routes of administration. Any person having an ordinary knowledge in the technical field to which the present invention belongs can determine any dosage form and dosing regimen depending on purpose of administration, routes of administration, severity of diseases and body weight.

The anti-osteoporotic composition of the present invention contains 4-{5-[4-(5-isopropyl-2-methyl-1,3-thiazol-4-yl) phenoxy]pentoxy}-benzamidine or N-hydroxy-4-{5-[4-(5-isopropyl-2-methyl-1,3-thiazol-4-yl)phenoxy]pentoxy}-benzamidine represented by the following formula 1 and its pharmaceutically acceptable carriers. The pharmaceutically acceptable carriers may include every type of standard pharmaceutical carriers used for the conventional dosage forms, such as sterile solution, tablet (including coated tablet) and capsules. The typical examples of such carrier include some excipients (e.g., starch, milk, sugar, specific clay, gelatin, stearic acid, talc, vegetable fat or oil, gum, glycols), or other conventional excipients. Such carriers may also include flavoring agents, color additives and other materials. The composition containing such carriers may be formulated by the conventional method.

The anti-osteoporotic composition of the present invention containing 4-{5-[4-(5-isopropyl-2-methyl-1,3-thiazol-4-yl) phenoxy]pentoxy}-benzamidine or N-hydroxy-4-{5-[4-(5-isopropyl-2-methyl-1,3-thiazol-4-yl)phenoxy]pentoxy}-benzamidine or its salts may be applied via the conventional routes of administration (e.g. oral, intravenous, intramuscular or transdermal) but not limited to these routes of administration.

A wide range of therapeutic doses of 4-{5-[4-(5-isopropyl-2-methyl-1,3-thiazol-4-yl)phenoxy]pentoxy}-benzamidine or N-hydroxy-4-{5-[4-(5-isopropyl-2-methyl-1,3-thiazol-4-yl)phenoxy]pentoxy}-benzamidine has been established for the prevention and treatment of osteoporosis. The therapeutic dose level for the treatment of osteoporosis is 10~1000 mg daily. Any person having an ordinary knowledge in the technical field to which the present invention belongs can determine the dose and dosing frequency depending on characteristics of an agent, severity of disease and body weight, size of inflammation and routes of administration.

BEST MODE FOR CARRYING OUT THE INVENTION

The present invention is explained in more detail by the following examples.

Example 1

Inhibitory Effects on Osteoclast Differentiation of Each Test Substance

The effect of each test substance on osteoclast proliferation and differentiation process were evaluated via co-culture with osteoblast.

1. Preparation of Cells
  a) Preparation of Bone Marrow Cells

Tibia and Femora were aseptically ectomized from male ddY mice of 6~8 weeks to harvest bone marrow cells by using a syringe (21G, Korea Green Cross).

The bone marrow cells were suspended in 5 mL α-MEM medium (Gibco BRL Co.) containing sodium bicarbonate (2.0 g/L), streptomycin (100 mg/L) and penicillin (100,000 unit/mL). The harvested cells were centrifuged at 800×g for 5 mins to collect the whole quantity. To remove the red blood cells within bone marrow cells, 3 mL of Tris HCl (0.83% NH$_4$Cl, pH7.5) was added and well mixed. After centrifuging above cells, the numbers of bone marrow cells were counted and then, the bone marrow cells were immediately used for co-culture system with osteoblast.

b) Preparation of Osteoblast

The calvaria were aseptically ectomized from neonate ICR mice of 1~2 days, washed with PBS solution and incubated with a mixture of enzyme solution (0.2% collagenase and 0.1% dispase) at 37° C. gentle shaker. This procedure was sequentially repeated (10, 10, 10, 20, 20 and 20 mins), and then the calvaria cells having the characteristics of osteoblast, were mostly released from III~VI digestion groups, were collected and washed with the medium (serum-free α-MEM). The washed cells were cultivated in α-MEM medium containing 10% FBS for 2~3 days. After subculturing, these cells were used for this experiment, and diluted to reach the concentration of 1×10$^6$ cells/mL for storage at −70° C.

2. Measurement of Osteoclast Differentiation
  a) Preparation of Specimen

N-hydroxy-4-{5-[4-(5-isopropyl-2-methyl-1,3-thiazol-4-yl)phenoxy]pentoxy}-benzamidine (DW1350) and 4-{5-[4-(5-isopropyl-2-methyl-1,3-thiazol-4-yl)phenoxy]pentoxy}-benzamidine (DW1352) used for test substances of the present invention, and N,N-diisopropyl-4-[4-(3-aminobenzo[d]isooxazole-6-yloxy)butoxy]-3-methoxybenzamide (hereinafter referred to as "HS-1141") and 4-[5-[4-(aminoiminomethyl)phenoxy]pentoxy]-3-methoxy-N,N-bis(1-methylethyl)benzamide maleic acid (Morrissey, M. M., Suh, H. U.S. Pat. No. 5,451,700; hereinafter referred to as "CGS-25019C"), LTB-4 receptor antagonists as control, were dissolved in a sterile distilled water to make desired concentrations following dilution. The volume of final specimen added to the medium was determined at the ratio of 1:1000.

b) Reaction with Specimens Via Co-Culture System

Bone marrow cells, so prepared from the above No. 1, and osteoblast from calvaria were co-cultured for osteoclast differentiation. Both bone marrow cells (25,000 cells/cm$^2$) and osteoblast (10,000 cells/cm$^2$) were plated on a 96 well plate in α-MEM medium containing 10% FBS with specimen, and then culture the reaction mixture for 7 days. Some differentiation factors, such as dexamethasone ($10^{-6}$M) and vitamin $D_3$ ($10^{-9}$M), were also continuously added to the medium from the first day of cultivation. The media were changed with fresh media containing a mixture of specimens and differentiation factors every 2~3 day.

c) Evaluation of Osteoclast Differentiation

1) Preparation of Tartarate Resistance Acid Phosphatase (TRAP) Staining Solution TRAP was used as a marker to measure osteoclast in consideration of its characteristics showing a positive reaction to TRAP staining solution. TRAP staining solution was prepared in a manner such that 5 mg of naphtol AS-MS phosphate (sigma N-4875), a substrate and 25 mg of coloring agent (Fast Red Violet LB salt) was dissolved in N,N-dimethylformamide (about 0.5 mL) and with the addition of 0.1N $NaHCO_3$ buffer solution (50 mL) containing 50 mM of tartaric acid, the reaction mixture was stored at refrigerator prior to use.

2) Staining Method

After 7-day culture, the medium was removed from the wells and then, the cells were once washed with PBS solution and fixed to PBS containing 10% formalin for 2~5 mins. The cells were also fixed in a mixed solution, ethanol and acetone (1/1), for about 1 min, and dried off. The cells were further treated by TRAP staining solution for 15 mins and washed with PBS to measure the experimental results with the staining degree of cells under a microscopic examination.

3) Analysis on the Experimental Results.

The counts of osteoclast only with more than 3 nuclei showing the TRAP-positive reaction were calculated under a microscopic examination, and each of test was reconfirmed over three times for gaining more reliable data.

As shown in the following table 1, the inhibitory effect of each experimental group on the differentiation of osteoclast versus controls were expressed by inhibitory percentage value, and 50% inhibitory concentration on osteoclast differentiation was calculated as $IC_{50}$.

The anti-osteoporotic effect of each test substance were compared with controls, such as CGS-25019C and HS-1141 (U.S. Pat. No. 6,150,390 and Korea Patent Application No. 98-3138), a conventional anti-osteoporotic agent belonging to the same member of CGS-25019C, which demonstrates the antagonistic action to the existing LTB-4 receptor.

TABLE 1

| Specimen | % inhibitory action | | | | $IC_{50}$ |
|---|---|---|---|---|---|
| | 3.2 nM | 16 nM | 80 nM | 400 nM | |
| DW1350 | 1.0 | 68.8 | 82.3 | 88.0 | 19.87 nM |
| DW1352 | 50.0 | 81.8 | 83.9 | 92.7 | 1.25 nM |
| HS-1141 | 1.2 | 3.0 | 12.0 | 23.5 | — |
| CGS-25019C | -8.9 | 8.3 | 0.0 | 17.7 | — |

As shown in the table 1, the experimental results indicate that the inhibitory effect of both DW1350 and DW1352 against osteoclast proliferation and differentiation were significantly better than those of HS-1141 and CGS-25019C. These test substances, which affect the osteoclast differentiation at a low concentration, may prove to be effective for the prevention and treatment of osteoporosis.

Example 2

Fusion Assay

This assay is designed to evaluate the influences of each test substance in terms of osteoclast fusion during the differentiation process in which immature prefusion osteoclasts (pOC; osteoclast structure with one more nuclei) were transformed into mature multinucleated osteoclast (OCL) via cell to cell fusion (Gregg Wesolowski et al. Experimental Cell Research 219, 679-686, 1995).

1. Preparation of Prefusion Osteoclast (pOC)

The prefusion osteoclast can be obtained via co-culture of both bone marrow cells and osteoblast, so prepared from Example 1. The mixture of both osteoblast (about $5 \times 10^5$ cells/plate) and bone marrow cells (about $1 \times 10^7$ cells/plate) were co-cultured in a 100 mm culture dish. Some differentiation factors, such as dexamethasone ($10^{-6}$M) and vitamin $D_3$ ($10^{-9}$M), were added to the medium from the first day of culture. The medium was changed with the fresh medium containing differentiation factors every 2 day.

Since a great number of the prefusion osteoclasts having one or more nuclei in fusion process were formed during 4-day co-culture, the cells were separated co-cultivation after 4 days. The medium was removed from the cells and with the addition of 0.2% collagenase solution (4 mL), the cells were incubated at 37° C. for 20 mins to separate the attachment cells. Since the majority of separated cells were osteoblasts, all osteoblasts were washed with PBS solution two or three times for their complete removal.

After the remaining prefusion osteoclasts were separated via reaction for 20 mins with the addition of echistatin containing 10% BSA, the cells were harvested by centrifuge.

2. Reaction of Fusion Experiment

The test substances diluted at each concentration were diluted at the desired concentration in α-MEM medium (addition of 10% FBS) to load them into a 96-well microplate in a dose of 100 μL per well. The osteoclastic monocytes, so separated from the preceding No. 1, were plated on a 96-well microplate in a dose of $5 \times 10^3$ cell/100 μL per well and cultured at 37° C. for 24 hrs, thus resulting in the osteoclast fusion successfully. In the case of specimen-free and positive controls, experiments were performed in the same manner as above. The positive control use for this experiment includes 4-{4-[4-(5-isopropyl-2-methyl-1,3-thiazol-4-yl)phenoxy]butoxy}-benzamidine (hereinafter referred to as "DW1351") and N-hydroxy-4-{4-[4-(5-isopropyl-2-methyl-1,3-thiazol-4-yl)phenoxy]butoxy}-benzamidine (hereinafter referred to as "DW1349") which have the similar chemical structure to HS-1141, CGS-25019C, DW1350 and DW1352.

3. Measurement of Osteoclast Fusion and its Analysis

The medium was removed from the cells and then, the cells were once washed with PBS once and fixed to PBS solution containing 10% formalin for about 5 mins. The cells were again fixed to both ethanol and acetone (1/1) in a mixing solution for about 5 mins and dried off. The cells were further treated by TRAP staining solution for 15 mins and washed with water to observe the cells under the microscope. The TRAP-positive osteoclast counts, which were differentiated from monocyte to multinucleated cells (osteoclast having more than 10 nuclei) via fusion process, were measured.

The following table 2 shows the differences of measured cell counts versus control as % inhibitory concentration.

TABLE 2

| Specimen | Inhibitory action (%) | | | | $IC_{50}$ |
|---|---|---|---|---|---|
| | 0.08 uM | 0.4 uM | 2 uM | 10 uM | |
| DW1350 | 4.50 | 25.64 | 80.00 | 97.95 | 0.81 uM |
| DW1352 | 5.13 | 24.72 | 87.18 | 98.97 | 0.74 uM |
| HS-1141 | 2.1 | 12.31 | 15.71 | 36.29 | — |

TABLE 2-continued

| | Inhibitory action (%) | | | | |
|---|---|---|---|---|---|
| Specimen | 0.08 uM | 0.4 uM | 2 uM | 10 uM | $IC_{50}$ |
| CGS-25019C | 10.14 | 13.04 | 13.77 | 12.32 | — |
| DW1351 | 0.0 | 0.0 | 38 | 74 | — |
| DW1349 | 0.0 | 2.3 | 4.5 | 18 | — |

As shown in the table 2, the experimental results demonstrate that both DW1350 and DW1352 exerted the significant inhibitory effects against osteoclast fusion ($IC_{50}$: 0.81 and 0.74 uM, respectively). More specifically, the inhibitory effects of both DW1350 and DW1352 against osteoclast fusion makes it possible to prevent the mature osteoclast formation which will result in the significant inhibition of osteoclast-dependent bone absorption. The control CGS-25019C showed little inhibitory effect against osteoclast fusion, irrespective of drug concentrations. The inhibitory effect of HS-1141 against osteoclast fusion was lower than those of DW1350 and DW1352, although the former was dependent on drug concentrations. In the case of DW1349 and DW1351 having extremely similar structure to DW1350 and DW1352, their inhibitory effects against osteoclast fusion were significantly lower than DW1350 and DW1352, although the former was dependent on drug concentrations like HS-1141.

Therefore, it is expected that among 4-[(4-thiazolyl)phenoxy]alkoxy-benzamidine derivatives, both DW1350 and DW1352 may be developed as new anti-osteoporotic agents by effectively inhibiting mature osteoclast formation based on the inhibitory mechanism of osteoclast fusion.

Example 3

Measurement of Bone Resorption (Pit Formation Assay)

The mature osteoclast (OCL) is mainly involved in removing mineral by bone resorption. This experiment is designed to measure the inhibitory effects of each test substance on the bone resorption of osteoclast using ivory fragment (Eijiro Jimi et al. Endocrinology 137, p 2187-2190, 1996).

1. Preparation of Mature Osteoclast
a) Preparation of Collagen Gel Solution

The co-culture system with for both bone marrow cells and osteoblast was performed using a cultivation dish containing collagen gel (cell matrix Type I-A). Collagen, 5-fold concentrated α-MEM medium and 0.05M NaOH buffer solution (2.2% $NaHCO_3$, pH7.4) were mixed at the ratio of 7:2:1 at a low temperature, and then storage at a low temperature. Then, 4 mL of the mixed solution was added to a 100 mm culture dish, applied evenly and left at 37° C. for 5 minutes.

b) Preparation of Mature Osteoclast Via Co-Culture System

Using α-MEM medium, the mixture of both bone marrow cells (about $1 \times 10^7$ cells/plate) and osteoblast (about $5 \times 10^5$ cells/plate), so separated from Example 1, were plated on a 100 mm dish containing collagen gel. The co-culture was performed in the presence of differentiation factors, such as vitamin D ($10^{-9}$M) and dexamethasone ($10^{-6}$M). As described above, a great number of mature multinucleated osteoclasts with the ability of bone resorption were obtained via 7-day co-culture. The medium was removed from the cells and with the addition of 0.2% collagenase solution, the attachment cells were separated by incubation for 20 minutes. The cells were collected via centrifuge. The harvested crude osteoclasts were again diluted in α-MEM medium to make the cells of 5,000 cells/100 μl.

2. Preparation of Hematoxylin Staining Solution

Hematoxylin staining solution was prepared in a manner such that made hematoxylin (1 g) was dissolved in 500 ml of distilled water and with the addition of 500 ml of distilled water and sodium iodide (0.2 g), the reaction mixture was stirred for 15 mins. Ammonium alum (50 g) and 7.5 ml of acetic acid were further added to the reaction mixture and filtered off.

3. Reaction on Ivory Fragment

After the ivory fragments, so cut with a thickness of 1 mm, were sterilized, each fragment was placed into a 96 well plate and then, 100 μl α-MEM medium (10% FBS) was added. To measure its inhibitory effect against the pit formation of osteoclast, each test substance was added in a maximum amount of 3 μl per concentration. With the addition of test substances, 100 μl of osteoclast solution was further added, mixed vigorously and cultured using 5% $CO_2$ incubator at 37° C. for 24 hrs. To observe the pits formed on the ivory fragments, the portion of grown osteoclast was directed upward and placed on a paper towel after removing them from the 96 well plate. With the removal of cells on the ivory, 10 μl of hematoxylin solution was dropped on the ivory to perform the staining for about 5 mins. The surface of ivory fragments was rubbed with a soft cotton pole to completely remove the staining solution.

4. Observation of Pits Formation and its Analysis

The following table 3 shows the number of pits on ivory fragment versus control as an inhibition percentage at various concentration under a microscopic examination.

TABLE 3

| | Inhibitory action (%) | | | | | |
|---|---|---|---|---|---|---|
| Specimen | 0.016 μM | 0.08 μM | 0.4 μM | 2 μM | 10 μM | $IC_{50}$ |
| DW1350 | 32.2 | 53.9 | 65.2 | 84.3 | 91.3 | 0.075 μM |
| DW1352 | 25.0 | 48.7 | 61.3 | 81.7 | 90.0 | 0.131 μM |
| HS-1141 | 9 | 33 | 50.4 | 75.3 | 88.7 | 0.421 μM |
| CGS-25019C | 0 | 0 | 2 | 9.2 | 17.3 | — |

As shown in the table 3, the experimental results demonstrate that both DW1350 and DW1352 exerted the significant inhibitory effect against the bone resorption of osteoclast. It also reveals that DW1350 and DW1352 had the $IC_{50}$ values of 0.075 μM and 0.131 μM, respectively, 3~6 times of inhibitory effect higher than HS-1141. In the case of CGS-25019C, a positive control, had a low inhibitory effect against the osteoclastic bone resorption.

Example 4

Evaluation of Alkaline Phosphatase (ALP) Activity to Measure Osteoblast Activity This experiment is designed to evaluate the differentiation and activity of osteoblast via ALP activity having a close relationship with osteoblastic bone formation (Y. Wada et al., Bone, 22, 479-485, 1998).

MC3T3-E1 cells (3,000 cells/well) derived from osteoblast were placed on a 96 well plate and after 24-hour culture, the media were changed with fresh medium containing various differentiation factors such as ascorbic acid (100 ug/ml) and β-glycerophosphatic acid (5 mM). The medium was also treated with test substances and the medium, containing differentiation factors and specimen, was changed with fresh medium every 3 days.

The culture was terminated after two weeks to measure ALP activity. With the removal of supernatant, 0.5% Triton X-100 were added for the lysis of cells. 100 µl of p-nitrophenylphosphate (1.21 mM) was added to 50 µl of above mixture. The mixture was incubated at 37° C. for 30 mins and with the addition of 0.2N sodium hydroxide (50 µl), the reaction was terminated. The standard curve was indicated at the absorbance of 405 nm using p-nitrophenol as a standard material and then, the absorbance of test substances, so reacted, was measured to observe the production amount of p-nitrophenol.

As shown in the following table 4, the units of ALP activity were determined as the amount of p-nitrophenol (nM) produced per time (per min or hour)/1 µg protein after measuring the amounts of protein contained in reaction mixture of each test substance.

TABLE 4

| Specimen ($10^{-8}$M) | ALP activity (units) |
| --- | --- |
| DW1350 | 19.8 |
| DW1352 | 17.1 |
| HS-1141 | 15.2 |
| CGS-25019C | 15.0 |
| Controls | 13.5 |

As shown in the table 4, the experimental results demonstrate that DW1350 exerted the highest ALP activity among all test substances. The ALP activities of DW1352 were also found to be superior to those of controls, HS-1141 and CGS-25019C. This experiment has indicated that both DW1350 and DW1352 were effective in stimulating osteoblast activity by affecting osteoblast differentiation and formation. Therefore, both DW1350 and DW1352 are quite useful drugs for the prevention and treatment of osteoporosis, since it can suppress the osteoclastic function, while stimulating the osteoblastic activity.

INDUSTRIAL APPLICABILITY

The aforementioned examples have revealed that both DW1350 and DW1352, a LTB-4 receptor antagonist, exert better inhibitory effect against osteoclast in terms of differentiation, formation, fusion and bone absorption.

Both agents may prove to be effective for the prevention and treatment of osteoporosis, since they can suppress the osteoclastic function with enhanced stimulation of osteoblastic activity, compared to DW1349 and DW1351 with the structural similarity, as well as HS-1141 and CGS-25019C.

Therefore, it is expected that the compound of the present invention may provide the basis for new osteoporosis therapies aimed at suppressing the osteoclastic bone sorption and stimulating the osteoblastic bone formation, including the treatment of LTB-4 related diseases.

The invention claimed is:

1. A method of treating osteoporosis in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Pit Formation Assay, without the addition of Leukotriene-$B_4$ ($LTB_4$), said compound inhibits osteoclast activity.

2. A method of inhibiting osteoclast activity and stimulating osteoblast activity in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Pit Formation Assay, without the addition of Leukotriene-$B_4$($LTB_4$), said compound inhibits osteoclast activity.

3. The method of claim 1 or 2, wherein in an in vitro Alkaline Phosphatase Assay, without the addition of Leukotriene-$B_4$ ($LTB_4$), said compound stimulates osteoblast activity.

4. The method of claim 1, wherein the compound is 4-{5-[4-(5-isopropyl-2-methyl-1,3-thiazol-4-yl)phenoxy]pentoxy}-benzamidine hydrochloride.

5. A method of treating osteoporosis in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Alkaline Phosphatase Assay, without the addition of Leukotriene-$B_4$($LTB_4$), said compound stimulates osteoblast activity.

6. A method of inhibiting osteoclast activity and stimulating osteoblast activity in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Alkaline Phosphatase Assay, without the addition of Leukotriene-$B_4$ ($LTB_4$), said compound stimulates osteoblast activity.

7. The method of claim 5 or 6, wherein in an in vitro assay selected from the group consisting of: Cell Fusion Assay, Tartarate Resistance Acid Phosphatase (TRAP) staining assay, and Pit Formation Assay, without the addition of Leukotriene-$B_4$($LTB_4$), said compound inhibits osteoclast activity.

8. The method of claim 5, wherein the compound is 4-{5-[4-(5-isopropyl-2-methyl-1,3-thiazol-4-yl)phenoxy]pentoxy}-benzamidine hydrochloride.

9. A method of treating osteoporosis in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Cell Fusion Assay, without the addition of Leukotriene-$B_4$($LTB_4$), said compound inhibits osteoclast activity.

10. A method of inhibiting osteoclast activity and stimulating osteoblast activity in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Cell Fusion Assay, without the addition of Leukotriene-$B_4$($LTB_4$), said compound inhibits osteoclast activity.

11. The method of claim 9 or 10, wherein in an in vitro Alkaline Phosphatase Assay, without the addition of Leukotriene-$B_4$($LTB_4$), said compound stimulates osteoblast activity.

12. The method of claim 9, wherein the compound is 4-{5-[4-(5-isopropyl-2-methyl-1,3-thiazol-4-yl)phenoxy]pentoxy}-benzamidine hydrochloride.

13. A method of treating osteoporosis in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Tartarate Resistance Acid Phosphatase (TRAP) Staining Assay, without the addition of Leukotriene-$B_4$($LTB_4$), said compound inhibits osteoclast activity.

14. A method of inhibiting osteoclast activity and stimulating osteoblast activity in a subject, the method comprising administering a composition comprising a compound, 4-{5-[4-(5-isopropyl-2-methyl-1,3-thiazol-4-yl)phenoxy]pentoxy}-benzamidine or a salt thereof to the subject in an amount effective to inhibit osteoclast activity and to stimulate osteoblast activity, wherein in an in vitro Tartarate Resistance Acid Phosphatase (TRAP) Staining Assay, without the addition of Leukotriene-$B_4$($LTB_4$), said compound inhibits osteoclast activity.

15. The method of claim 13 or 14, wherein in an in vitro Alkaline Phosphatase Assay, without the addition of Leukotriene-$B_4$($LTB_4$), said compound stimulates osteoblast activity.

16. The method of claim 13, wherein the compound is 4-{5-[4-(5-isopropyl-2-methyl-1,3-thiazol-4-yl)phenoxy]pentoxy}-benzamidine hydrochloride.

* * * * *